United States Patent [19]

Labroo et al.

[11] Patent Number: 5,464,862
[45] Date of Patent: * Nov. 7, 1995

[54] METHOD FOR INHIBITING BONE LOSS USING CENTCHROMAN DERIVATIVES

[75] Inventors: Virender M. Labroo, Mill Creek; James R. Piggott, Bothell; Steven D. Bain, Seattle, all of Wash.

[73] Assignee: ZymoGenetics, Inc., Seattle, Wash.

[*] Notice: The portion of the term of this patent subsequent to Jan. 18, 2011, has been disclaimed.

[21] Appl. No.: 180,728

[22] Filed: Jan. 13, 1994

Related U.S. Application Data

[63] Continuation-in-part of Ser. No. 29,729, Mar. 11, 1993, Pat. No. 5,280,040.

[51] Int. Cl.$^6$ .................................................. A61K 31/40
[52] U.S. Cl. ........................ 514/422; 514/410; 514/411; 514/428; 514/456
[58] Field of Search ................................. 514/422, 456, 514/428, 410, 411

[56] References Cited

U.S. PATENT DOCUMENTS

| | | | |
|---|---|---|---|
| 3,340,276 | 9/1967 | Carney et al. | 260/345.2 |
| 3,822,287 | 7/1974 | Bolger et al. | 260/326.5 |
| 4,210,644 | 7/1980 | Ewing et al. | 424/239 |
| 4,447,622 | 5/1984 | Salman et al. | 548/525 |
| 4,489,056 | 12/1984 | Himmelstein et al. | 424/22 |
| 4,644,012 | 2/1987 | Tsuda et al. | 514/456 |
| 4,882,347 | 11/1989 | Cozzi et al. | 514/396 |
| 4,902,679 | 2/1990 | Benedict et al. | 514/86 |
| 5,015,661 | 5/1991 | Walser | 514/443 |
| 5,063,234 | 11/1991 | Bryant et al. | 514/288 |
| 5,280,040 | 1/1994 | Labroo et al. | 514/422 |
| 5,317,029 | 5/1994 | Inazu et al. | 514/422 |

OTHER PUBLICATIONS

Johri et al., *Contraception* 44(5):549–557, 1991.
Salman et al., *J. Med. Chem.* 26:592–595, 1983.
Ray et al., *J. Med. Chem.* 19(2):276–279, 1976.
Kumari et al., *Contraception* 13(6):665–676, 1976.
Singh et al., *Chem. Abstr.* 117(7):63184t, 1992.
Kamboj et al., *Chem. Abstr.* 88(15):99512v, 1977.
Broulik, *Endocrine Regulations* 25:217–219, 1991.
Liu, *J. Bone Min. Res. Abstr.* 5(Suppl.2):S249, 1990.
Stewart et al., *Endocrinology* 118:125–131, 1986.
Beall et al., *Calcif. Tissue Int.* 36:123–125, 1984.
Jordan et al., *Breast Cancer Research and Treatment* 10:31–35, 1987.
Salman et al., *J. Med. Chem.* 29:1801–1803, 1986.

*Primary Examiner*—Marianne M. Cintins
*Assistant Examiner*—T. J. Criares
*Attorney, Agent, or Firm*—Gary E. Parker; Deborah A. Sawislak

[57] ABSTRACT

Methods and pharmaceutical compositions for reducing bone loss are disclosed. 3,4-diarylchromans and their pharmaceutically acceptable salts are formulated into medicaments for the treatment of bone loss due to osteoporosis or other conditions. An exemplary 3,4-diarylchroman is centchroman (3,4-trans-2,2-dimethyl-3-phenyl-4-[ p-(beta-pyrrolidinoethoxy)phenyl]-7-methoxychroman). Formulations include tablets and other forms suitable for oral administration and controlled-release subdermal implants.

24 Claims, 3 Drawing Sheets

*P<.05 decreased compared to sham animals treated with vehicle and ovx mice treated with centchroman; n = 8 mice/group.

METHOD FOR INHIBITING BONE LOSS USING CENTCHROMAN DERIVATIVES

CROSS-REFERENCE TO RELATED APPLICATION

This application is a continuation-in-part of Ser. No. 08/029,729, filed Mar. 11, 1993, now U.S. Pat. No. 5,280,040.

BACKGROUND OF THE INVENTION

Bone remodeling is the dynamic process whereby skeletal mass and architecture are renewed and maintained. This renewal and maintenance is a balance between bone resorption and bone formation, with the osteoclast and the osteoblast considered the two key participants in the remodeling process. The osteoclast initiates the remodeling cycle by resorbing a cavity in the bone which is subsequently refilled when the osteoblast synthesizes and deposits new bone matrix into the excavation. The activities of osteoclast and osteoblast are regulated by complex interactions between systemic hormones and the local production of growth factors and cytokines at active remodeling sites.

Imbalances in bone remodeling are associated with such conditions as osteoporosis, Paget's disease, and hyperparathyroidism. Osteoporosis, characterized by a decrease in the skeletal mass, is one of the most common diseases of postmenopausal women and is often the cause of debilitating and painful fractures of the spine, hip and wrist.

Approximately 25% of all postmenopausal women suffer from osteoporosis, and it is generally accepted that the etiology of the disease involves the reduction of circulating estrogens (Komm et al., *Science* 241:81–84, 1988). Komm et al. further report that the proportion of caucasian women in the United States who are at risk for a hip fracture is 15%, or 247,000 hip fractures per year in women over the age of 45.

The costs of osteoporosis, both personal and financial, are enormous. In 1984, 145,000 in-patient fracture reductions and 107,000 hip arthroplasties and replacements were performed on American women over 65 years of age. Among patients who lived alone prior to hip fracture, 15% to 20% required long-term care as a result of the fracture and one year after the fracture had still not regained their independence. The total financial cost of osteoporosis treatment, including fractures, in the United States in 1986 was 7–10 billion dollars (Peck et al., *Am. J. Med.* 84:275–282, 1988).

Bone loss associated with osteoporosis has been arrested by the administration of exogeneous estrogens. To be effective, estrogen therapy must begin within a few years of the onset of menopause, and should continue for 10 to 15 years, according to Thorneycroft (*Am. J. Obstet. Gynecol.* 160:1306–1310, 1989). While there are several different types of estrogens, 17-β-estradiol is the primary estrogen found naturally occurring in premenopausal women and is often the compound of choice for therapeutic use. At the recommended dose, however, there are significant side effects, the most disturbing being the well-established correlation of estrogen therapy with endometrial and breast cancers. The incidence of carcinoma is both dose-dependent and duration-dependent.

Avoidance of the cancer risk has been achieved by the concomitant use of a progestogen with estrogen. This combination, however, causes menses to return, which many women find unacceptable. A further disadvantage is that the long-term effects of the progestogen have not been fully determined. Thus, a large population of women require alternatives to hormone replacement therapies that can safely prevent the rapid bone loss that accompanies the menopause.

Centchroman is a non-steroidal compound known to have antiestrogenic activity. It is in use in India as an oral contraceptive (see, for example, Salman et al., U.S. Pat. No. 4,447,622; Singh et al., *Acta Endocrinal (Copenh)* 126:444–450, 1992; Grubb, *Curr. Opin. Obstet. Gynecol.* 3:491–495, 1991; Sankaran et al., *Contraception* 9:279–289, 1974; Indian Patent No. 129187). Centchroman has also been investigated as an anti-cancer agent for treatment of advanced breast cancer (Misra et al., *Int. J. Cancer* 43:781–783, 1989), but has not previously been shown to have an effect on bone resorption.

There remains a need in the art for compositions and methods useful in reducing bone loss, in particular bone loss associated with osteoporosis. There is a further need for such compositions that lack the undersirable side effects of estrogens. The present invention provides such compositions and methods and also provides other, related advantages.

DETAILED DESCRIPTION OF THE INVENTION

Figure 1:
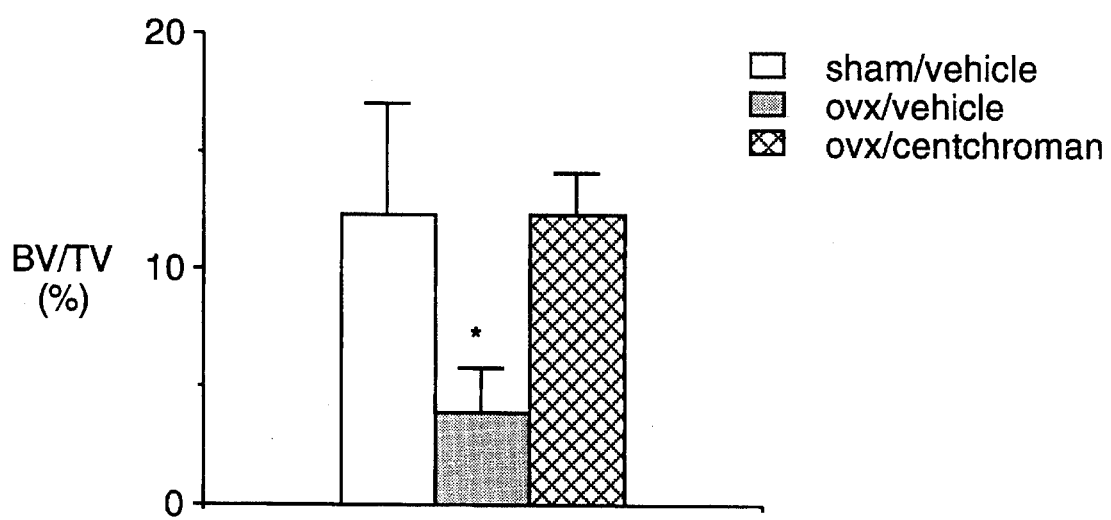
FIG. 1 illustrates the effects of centchroman on bone loss in ovariectomized mice.

The present invention is based in part on the discovery that a representative 3,4-diarylchroman, centchroman (3,4-trans-2,2-dimethyl-3-phenyl-4-[p-(betapyrrolidinoethoxy)phenyl]- 7-methoxy-chroman), is an effective inhibitor of bone loss in ovariectomized mice and rats. These animal models mimic the post-menopausal condition and are generally recognized models of osteoporosis. These data thus indicate that the 3,4-diarylchromans are useful as therapeutic agents for reducing bone loss in mammals, including primates such as humans.

Within the present invention, compounds of formula (I) or their pharmaceutically acceptable salts are used for reducing bone loss in a patient.

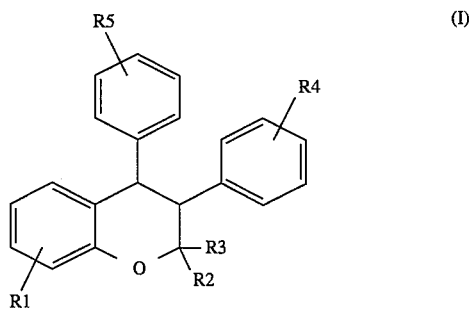

Within formula (I), R1, R4 and R5 are individually hydrogen, halo, trifluoromethyl, lower alkyl, lower alkoxy or tertiary amino lower alkoxy; and R2 and R3 are individually H or a lower alkyl. As used herein, the term "lower alkyl" includes straight and branched chain alkyl radicals containing from 1 to 6 carbon atoms, such as methyl, ethyl, n-propyl, isopropyl, n-butyl, tertbutyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, n-propoxy, isopropoxy, n-butoxy, tert-butoxy, n-ethoxy, amyloxy, sec-amyloxy, n-hexyloxy, 2-ethyl-butoxy, 2,3-dimethylbutoxy and the like. "Halo" includes chloro, fluoro, bromo and iodo. The tertiary amino radical may be a dialkylamine such as a dimethyl, diethyl, dipropyl, dibutyl or a polymethyleneimine, e.g. piperidine, pyrrolidine, N-methyl piperazine or morpholine. Preferred compounds include those in which R1 is lower alkoxy; R2 and R3 are lower alkyl, especially methyl; R4 is H; and R5 is tertiary amino lower alkoxy of the polymethyleneimine type. Within particularly preferred embodiments, R1 is in the 7-position and is lower alkoxy, particularly methoxy; each of R2 and R3 is methyl, R4 is H and R5 is in the 4-position and is a tertiary amino lower alkoxy radical such as pyrrolidinoethoxy.

It is preferred to use the compounds of structure (I) in the trans configuration. These compounds may be used as racemic mixtures, or the isolated d- or l-enantiomers may be used.

A particularly preferred compound for use within the present invention is centchroman (II):

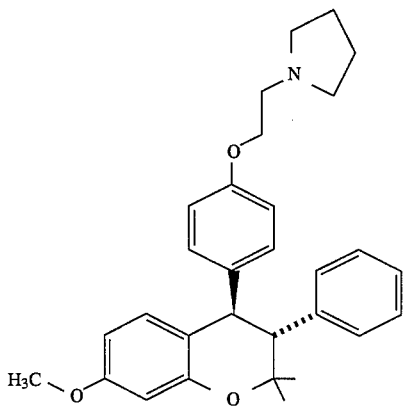

(II)

Although only one enantiomer is shown, it will be understood that the structure II is used herein to designate the trans configuration of the 3- and 4-phenyl groups and that both the d- and l-enantiomers, as well as the racemic mixture, are included.

3,4-diarylchromans are prepared according to known methods, such as those disclosed in U.S. Pat. No. 3,340,276 to Carney et al., U.S. Pat. No. 3,822,287 to Bolger, and Ray et al., *J. Med. Chem.* 19:276–279, 1976, which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer.

Within the present invention, 3,4-diarylchromans may be prepared in the form of pharmaceutically acceptable salts, especially acid-addition salts, including salts of organic acids and mineral acids. Examples of such salts include salts of organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans and their salts are useful within human and veterinary medicine for the regulation of bone metabolism. These compounds may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

For use within the present invention, 3,4-diarylchromans and their pharmaceutically acceptable salts are formulated with a pharmaceutically acceptable carrier to provide a medicament for parenteral, oral, nasal, rectal, subdermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release subdermal implants, tablets, etc. One skilled in this art may formulate the compounds in an appropriate manner, and in accordance with accepted practices, such as those disclosed in *Remington's Pharmaceutical Sciences,* Gennaro, ed., Mack Publishing Co., Easton, Pa., 1990 (which is incorporated herein by reference in its entirety.)

Oral adiministration is preferred. Thus, the active compound is prepared in a form suitable for oral administration, such as a tablet or capsule. Typically, a pharmaceutically acceptable salt of the compound is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, coloring, etc.

Pharmaceutical compositions are administered at daily to weekly intervals. An "effective amount" of such a pharmaceutical composition is the amount that provides a clinically significant inhibition of bone loss. Such amounts will depend, in part, on the particular condition to be treated, age, weight, and general health of the patient, and other factors evident to those skilled in the art. In general, inhibition of bone loss is manifested as a statistically significant difference in cancellous bone volume between treatment and control groups. This can be seen as, for example, a 5–10% or more difference in spinal bone mass or bone mineral content over two years. Data from accepted animal models, such as the ovariectomized mouse or rat models of osteoporosis, are generally predictive of doses in humans to within one order of magnitude. For example, therapeutic doses for the treatment of osteoporosis will generally range from 0.01–50 mg/kg/day, preferably 0.05–10 mg/kg/day, most preferably 0.1–5.0 mg/kg/day. The use of cis-isomers or racemic mixtures may necessitate doses in the higher end of the stated range.

The pharmaceutical compositions may be administered in unit dosage form on a daily to weekly basis. In the alternative, they may be provided as controlled release formulations suitable for subdermal implantation. Implants are formulated to provide release of active compound over the desired period of time, which can be up to several years. Controlled-release formulations are disclosed by, for example, Sanders et al., *J. Pharm. Sci.* 73: 1294–1297, 1984; U.S. Pat. No. 4,489,056; and U.S. Pat. No. 4,210,644, which are incorporated herein by reference.

The following examples are offered by way of illustration, not limitation.

EXAMPLE 1

The ability of centchroman to prevent osteopenia induced by estrogen deficiency was evaluated in the ovariectomized mouse model. Twenty-four female Swiss-Webster mice (8 weeks old) received either an ovariectomy or sham surgery prior to the initiation of a 4 week treatment protocol. For the ovariectomy, a flank incision through the skin, muscle and abdominal peritoneum was made on each side, the ovaries were located and dissected free of adherent fat and connective tissue, and excised. In the sham procedure the ovaries were exteriorized and replaced. In all animals the peritoneum and muscle were sutured together and the skin incisions were closed with wound clips.

Centchroman was dissolved in a minimal amount of dimethylsulfoxide and diluted in oil vehicle to a concentration of 50 µg/100 µl. The mice were treated twice per week for 4 weeks with a subcutaneous injection of centchroman or oil vehicle according to the following outline: Sham/oil vehicle (SV); OVX/oil vehicle; OVX/50 µg centchroman two times per week. There were 8 animals in each group.

At the conclusion of the 4-week centchroman treatment, the mice were anesthetized with ether and sacrificed by cervical dislocation. Immediately after sacrifice, the femurs were removed and fixed in 70% ethyl alcohol (EtOH) and dehydrated in a series of increasing alcohol concentrations: 95% EtOH for 24 hours followed by three changes in 100% EtOH of 24 hours each. After the final 100% EtOH the femurs were cleared in two changes of xylene and then processed undecalcified and embedded in methacrylate plastic according to previously described methods (Bain et al., *Stain Technology* 65: 159–163, 1990). Frontal sections of the distal metaphyses of the femur 5 µm thick were cut on a Reichert-Jung 2050 rotary microtome equipped with a tungsten-carbide knife. The 5 µm sections were mounted on glass slides and stained with Goldner's trichrome stain.

Histomorphometric measurements of the distal metaphyses were determined using the Bioquant Bone Morphometry Program (Biometrics, Inc., Nashville, Tenn.) interfaced via a camera lucida with an Olympus BH-2 light/epifluorescent microscope (Scientific Instruments, Inc., Redmond, Wash.). Morphometric measurements of cancellous bone volume (BV/TV) were performed in the tissue space greater than 0.25 mm from the growth plate-metaphyseal junction to exclude primary spongiosa.

Data, shown in FIG. 1, are expressed as the mean ± SD for each group. Comparison of cancellous bone volumes of the distal femur were based on analysis of variance using Statview® statistical programs (Abacus Concepts, Inc., Berkeley, Calif.). Treatment differences indicated by the ANOVA were compared using Dunnett's multiple comparison procedure. A P value of less than 0.05 was considered significant.

In ovariectomized mice treated with oil vehicle a 50% decrease in the cancellous bone volume of the distal femur compared to sham animals treated with vehicle was observed. In the ovariectomized animals treated with 50 µg of centchroman twice per week this bone loss was completely prevented.

EXAMPLE 2

To evaluate centchroman effects on bone resorption and bone mass, the skeletons of 54 female Sprague-Dawley rats were pre-labeled over four consecutive weeks with tritiated tetracycline ($^3$H-T; obtained from Dupont NEN Research Products, Boston, Mass.). Animals were given 12–15 injections of 15 µCi each for a total of approximately 200 µCi per animal. Three days after the final $^3$H-T injection, eight animals were sacrificed as baseline controls, and the remaining animals were randomized for estrogen (E2) or centchroman (C) treatments according to the following outline: sham/placebo; ovariectomy(ovx)/placebo; ovariectomy/E2 (0.05 mg/kg/day); ovariectomy/C (0.05 mg/kg/day); ovariectomy/C (0.5 mg/kg/day); and ovariectomy/C (5.0 mg/kg/day). The hormone treatments were delivered via subcutaneous pellet implants containing a matrix of cholesterol, lactose, celluloses, phosphatases and stearates (Innovative Research, Toledo, Ohio) calculated to deliver the doses indicated above. In addition to the quantification of bone resorption using the $^3$H-T assay, the bone mass of femurs and vertebrae were also determined to document changes in bone physical properties, and quantitative histomorphometry was used to compare changes in cancellous bone volumes of the proximal tibiae.

Sixty days after the initiation of the treatment protocols, the animals were anesthetized with ether and sacrificed by cervical dislocation. Immediately after sacrifice, the uteri were removed and weights recorded; both femurs and three thoracic vertebrae (T11–T13) were excised for the bone resorption assay; one tibia and the first lumbar vertebra were collected for determination of bone physical properties; and the second tibia was excised and processed for bone histomorphometry. All tissues were fixed initially in 70% ethyl alcohol (EtOH) and dehydrated in an ascending series of EtOH to 100%. After the final change of 100% EtOH, the specimens were processed according to the assay protocols outlined below.

The assay of whole bone resorption was based on the levels of 3H-T retained in the pre-labeled femurs and vertebrae essentially as disclosed by Klein and Jackman (*Calcified Tissue Research* 20: 275–290, 1976). Briefly, the samples were defatted in three changes of chloroform of 24 hours each and dried at 100° C. for 24 hours, and the weights were recorded. To extract the 3H-T, the femurs and vertebrae were demineralized in 15 ml of 0.5 N hydrochloric acid (HCl), and the supernatants were decanted and reserved. To quantify tritium levels, 625 µl aliquots were pipetted into glass scintillation vials containing 10 ml of Optiflor scintillation fluid (Packard Instruments, Meriden, Conn.), and the $^3$H-T levels were counted on a liquid scintillation spectrometer (Beckman LS 1800).

Following the EtOH dehydration, the samples for measuring bone mass were defatted in three changes of chloroform of 24 hours each and dried in a 60° C. oven overnight. Bone mass was expressed as mg of dry weight per gram of body weight.

After the final 100% EtOH treatment, the tibiae were cleared in two changes of xylene, processed undecalcified and embedded in methacrylate plastic essentially as disclosed by Bain et al. (*Stain Technology* 65: 159–163, 1990). Frontal sections of the proximal tibiae 5 μm thick were cut on a Reichert-Jung 2050 rotary microtome (Leica Instruments, Nusslock, Germany) equipped with a tungsten carbide knife. The 5 μm sections were stained with Goldner's trichrome stain.

Histomorphometric measurements of the proximal tibiae were determined using a Bioquant Bone Morphometry program (Biometrics, Inc., Nashville, Tenn.) interfaced via a camera lucida with an Olympus BH-2 light/epifluorescent microscope (Scientific Instruments, Inc., Redmond, Wash.). Morphometric measurements of cancellous bone volume (cn. BV/TV) were performed in a 3.0 mm² tissue space 1.5 millimeters from the growth plate-metaphyseal junction to exclude measurements of primary spongiosa. A minimum of four separate sections were measured from each animal.

Analyses of uterine weights, bone resorption assays, bone physical properties and bone histomorphometry were based on analysis of variance (ANOVA) using Statview® statistical programs (Abacus Concepts, Inc., Berkeley, Calif.). When significance was indicated by the ANOVA, control and treatment means were compared using Dunnett's multiple comparison procedure. P values of less than 0.05 were considered significant.

Compared to sham-vehicle treated animals, ovariectomy led to significant decreases in uterine wet weights. Estrogen replacement restored uterine weights to sham values, but centchroman treatment had no statistically significant effect on uterine weight, even at the highest dose of 5.0 mg per day. Indicative of increased bone resorption, ovariectomy reduced the skeletal retention of $^3$H-T in femurs and vertebrae (Tables 1 and 2, respectively). As expected, estrogen treatment increased the skeletal retention of $^3$H-T. Centchroman mimicked the effect of estrogen on bone resorption by causing a dose-dependent increase in the skeletal retention of $^3$H-T at both skeletal sites ($r^2$ values equal 0.96 and 0.92 for femora and vertebrae, respectively).

TABLE 1

Retention of $^3$H-T in Femurs

| Group | Count | cpm (thousands) | |
|---|---|---|---|
| | | Mean | Std. Dev. |
| sham/placebo | 8 | 3832.25 | 928.975 |
| ovx/placebo | 8 | 3184.375 | 680.598 |
| ovx/0.05 mg E2 | 10 | 4782 | 1501.813 |
| ovx/0.05 mg C | 9 | 3373.556 | 733.896 |
| ovx/0.5 mg C | 10 | 3405.1 | 1107.792 |
| ovx/5.0 mg C | 9 | 4192.222 | 1107.3 |

TABLE 2

Retention of $^3$H-T in Vertebrae

| Group | Count | cpm (thousands) | |
|---|---|---|---|
| | | Mean | Std. Dev. |
| sham/placebo | 8 | 1876.75 | 481.552 |
| ovx/placebo | 8 | 1531.625 | 416.205 |
| ovx/0.05 mg E2 | 9 | 2467.556 | 733.064 |
| ovx/0.05 mg C | 9 | 1523.333 | 406.635 |
| ovx/0.5 mg C | 10 | 1616 | 509.954 |
| ovx/5.0 mg C | 10 | 2156.7 | 495.741 |

Figure 2:
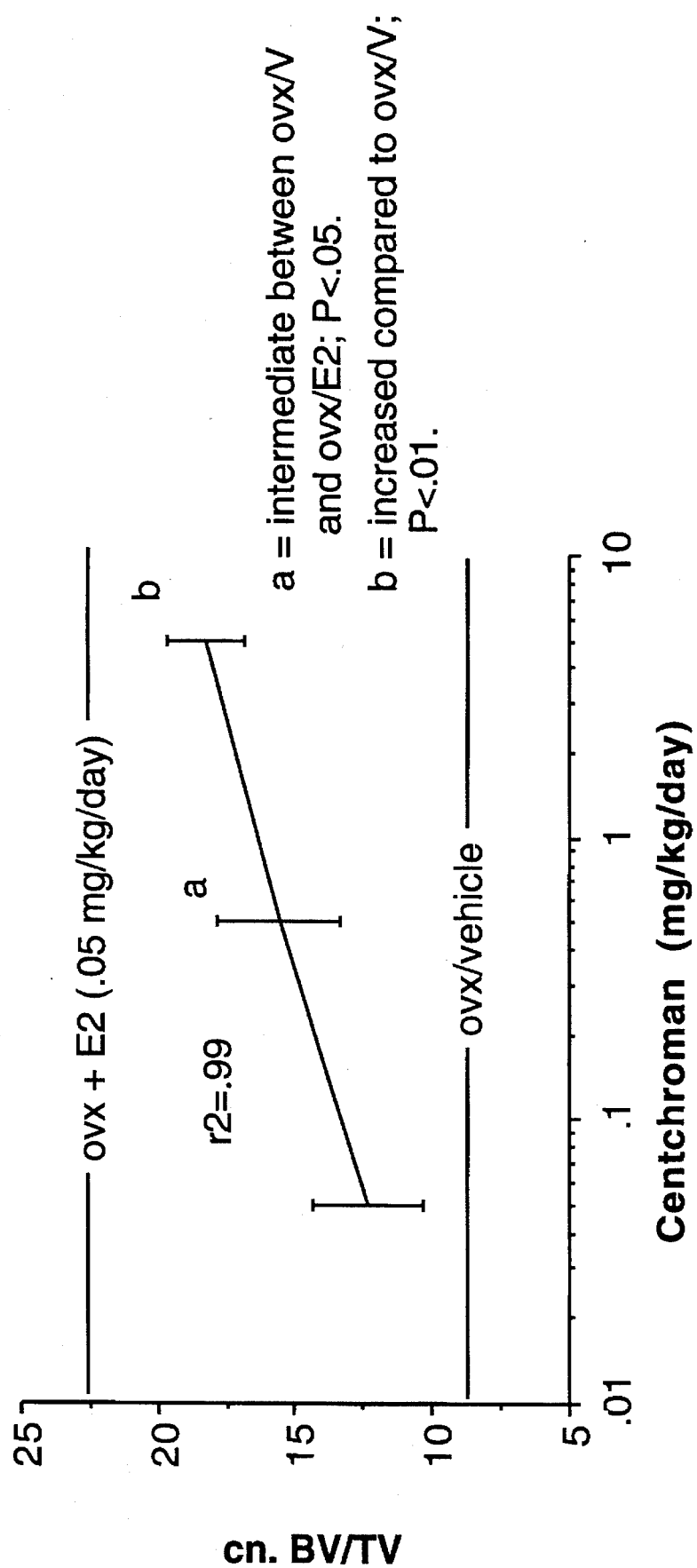
FIG. 2 illustrates the effects of centchroman on cancellous bone volumes in the proximal tibiae of ovariectomized rats.

The ability of centchroman to inhibit bone resorption and prevent bone loss was confirmed by measurements of cancellous bone volume in the tibiae and bone mass determinations of femora and vertebrae. Compared to ovariectomized rats treated with vehicle, centchroman caused a dose-dependent increase in cancellous bone volume of the proximal tibiae (FIG. 2; $r^2$=0.99). Similarly, centchroman had dose-dependent effects on bone mass in femora and vertebrae.

Figure 3:
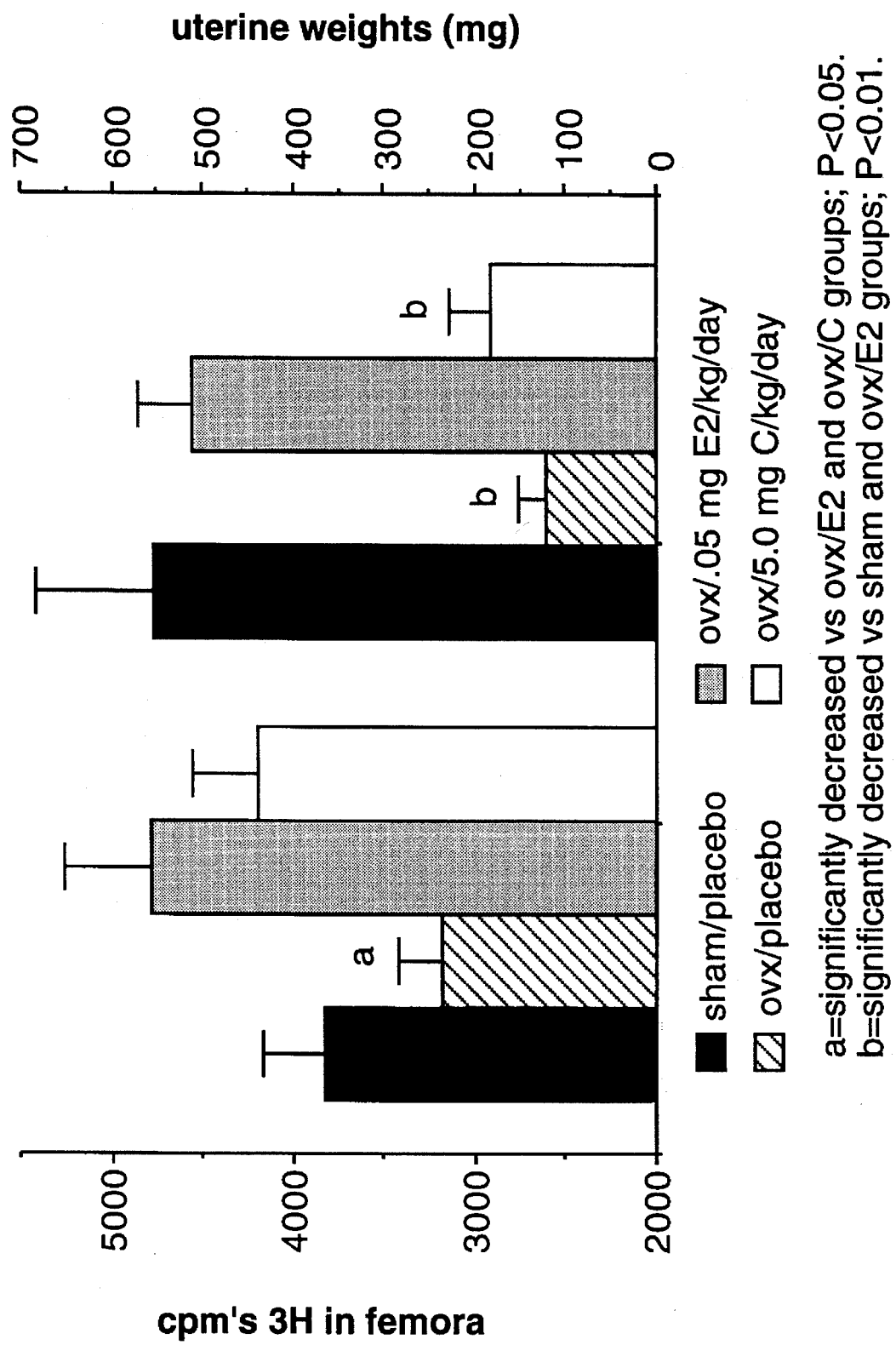
FIG. 3 illustrates the effects of centchroman on bone resorption (left) and uterine weights (right) in ovariectomized rats.

In summary, these data indicate that the ability of centchroman to prevent bone loss in the ovariectomized rat is independent of any apparent uterotrophic activity. This is clearly demonstrated in FIG. 3 by combining uterine weight data with the bone resorption data from the femur to show the independent effects of centchroman on these two tissues.

Although the foregoing invention has been described in some detail by way of illustration and example for purposes of clarity of understanding, it will be evident that certain changes and modifications may be practiced within the scope of the appended claims.

We claim:

1. A method for reducing bone loss in a patient comprising administering to a patient suffering from bone loss due to osteoporosis, Paget's disease or hyperparathyroidism an effective amount of a composition comprising a bone loss inhibiting compound of the formula

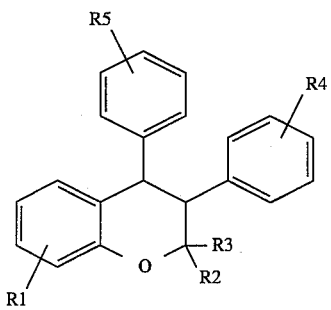

or a pharmaceutically acceptable salt thereof, wherein

R1, R4 and R5 are individually hydrogen, hydroxy, halo, trifluoromethyl, lower alkyl, lower alkoxy or tertiary amino lower alkoxy; and R2 and R3 are individually hydrogen or lower alkyl, in combination with a pharmaceutically acceptable carrier.

2. A method according to claim 1 wherein R1 is lower alkoxy, R2 and R3 are lower alkyl, R4 is hydrogen and R5 is tertiary amino lower alkoxy.

3. A method according to claim 1 wherein R1 is methoxy.

4. A method according to claim 1 wherein R2 and R3 are methyl.

5. A method according to claim 1 wherein R4 is hydrogen.

6. A method according to claim 1 wherein R5 is

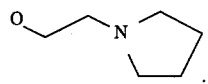

7. A method according to claim 1 wherein said compound is an isolated d- or l-enantiomer.

8. A method according to claim 1 wherein said compound is

9. A method according to claim 1 wherein said compound is

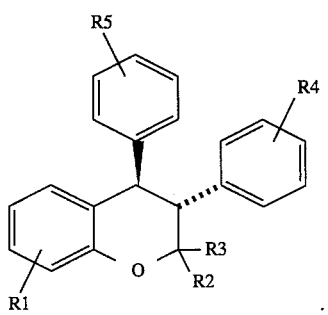

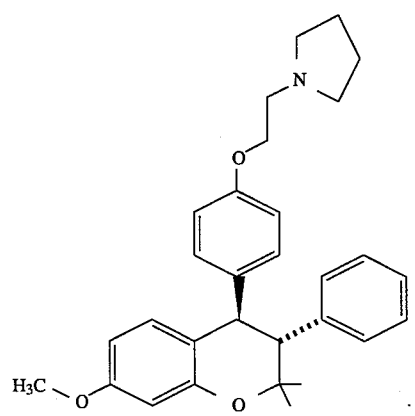

10. A method according to claim 9 wherein said compound is an isolated d- or l-enantiomer.

11. A method according to claim 1 wherein said patient is a post-menopausal female.

12. A method according to claim 1 wherein said composition is in a form suitable for oral administration.

13. A method according to claim 1 wherein said compound is administered at a dose of 0.1–5.0 mg/kg patient weight/day.

14. A method according to claim 1 wherein said composition is administered at daily to weekly intervals.

15. A method according to claim 1 wherein said composition is in the form of a subdermal implant.

16. A method for treating osteoporosis comprising administering to a patient an isolated d- or l-enantiomer of a bone loss inhibiting compound of the formula

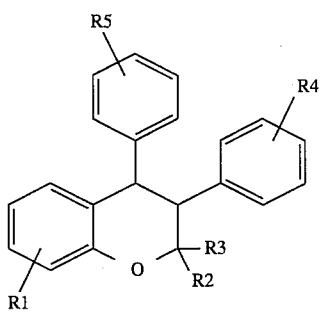

or a pharmaceutically acceptable salt thereof, wherein

R1, R4 and R5 are individually hydrogen, hydroxy, halo, trifluoromethyl, lower alkyl, lower alkoxy or tertiary amino lower alkoxy; and R2 and R3 are individually hydrogen or lower alkyl, in an amount sufficient to inhibit bone resorption.

17. A method according to claim 16 wherein R1 is lower alkoxy, R2 and R3 are lower alkyl, R4 is hydrogen and R5 is tertiary amino lower alkoxy.

18. A method according to claim 16 wherein R1 is methoxy.

19. A method according to claim 16 wherein R2 and R3 are methyl.

20. A method according to claim 16 wherein R4 is hydrogen.

21. A method according to claim 16 wherein R5 is

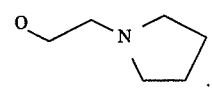

22. A method according to claim 16 wherein said compound is

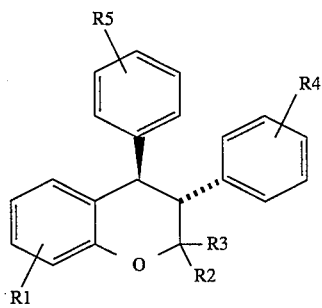

23. A method according to claim 16 wherein said compound is

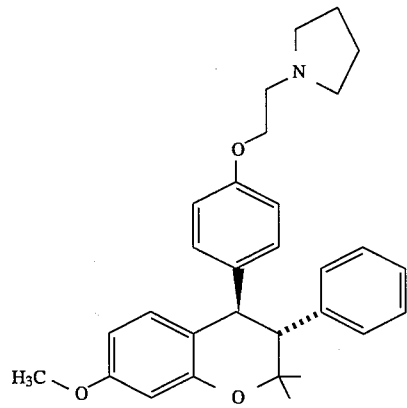

24. A method according to claim 16 wherein said patient is a post-menopausal female.

* * * * *

UNITED STATES PATENT AND TRADEMARK OFFICE
CERTIFICATE OF CORRECTION

PATENT NO. : 5,464,862
DATED : November 7, 1995
INVENTOR(S) : Virender M. Labroo et al.

It is certified that error appears in the above-indentified patent and that said Letters Patent is hereby corrected as shown below:

On the title page: Notice [*], in the second line, please delete "Jan. 18, 2011" and insert therefor, -- March 11, 2013 --.

Signed and Sealed this

Ninth Day of December, 1997

Attest:

BRUCE LEHMAN

*Attesting Officer*  *Commissioner of Patents and Trademarks*